United States Patent [19]

Tsujii et al.

[11] Patent Number: 4,762,928

[45] Date of Patent: Aug. 9, 1988

[54] AMINO-TRIFLUOROMETHYLPYRIDINE COMPOUND

[75] Inventors: Yasuhiro Tsujii; Tatsuo Isogai; Takao Awazu; Hisayoshi Jyonishi; Tokiya Kimura, all of Kusatsu, Japan

[73] Assignee: Ishihara Sangyo Kaisha Ltd., Osaka, Japan

[21] Appl. No.: 943,004

[22] Filed: Dec. 18, 1986

[30] Foreign Application Priority Data

Dec. 27, 1985 [JP] Japan ............................... 60-295171

[51] Int. Cl.$^4$ ........................................... C07D 213/73
[52] U.S. Cl. .................................. 546/311; 546/306; 546/312
[58] Field of Search ........................................ 546/311

[56] References Cited

U.S. PATENT DOCUMENTS

| | | | |
|---|---|---|---|
| 3,681,369 | 8/1972 | Doherty | 71/94 |
| 3,787,420 | 1/1974 | Torba | 546/311 |
| 3,830,822 | 8/1974 | Barlow et al. | 546/311 |
| 4,349,681 | 9/1982 | Yokomichi et al. | 546/304 |

OTHER PUBLICATIONS

Chemical Abstracts, 106:102316g.
CA, 101:38312b, (1984).

Primary Examiner—Mary C. Lee
Assistant Examiner—Dale A. Bjorkman
Attorney, Agent, or Firm—Sughrue, Mion, Zinn, Macpeak, and Seas

[57] ABSTRACT

A novel amino-trifluoromethylpyridine compound selected from the group consisting of 3-amino-5-trifluoromethylpyridine, 2-amino-4-trifluoromethylpyridine, and 2-amino-4,6-bis(trifluoromethyl)pyridine, and, a process for preparing the same by reacting a halogeno-trifluoromethylpyridine compound with ammonia at a temperature of 50° to 200° C. The compound is useful as an intermediate from which a compound effective in controlling various harmful organisms or an effective component compound of medicines can be easily derived.

4 Claims, No Drawings

AMINO-TRIFLUOROMETHYLPYRIDINE COMPOUND

BACKGROUND OF THE INVENTION

The present invention relates to a novel amino-trifluoromethylpyridine compound as an intermediate from which a compound effective in controlling various harmful organisms or an effective component compound of medicines can be easily derived, and a process for preparing the same.

A number of pyridine derivatives have hitherto been known to be useful intermediates for the production of organic compounds. For example, 2-amino-5-trifluoromethylpyridine as a starting material for the production of imidazopyridines and a process for the production thereof from 5-carboxy-2-hydroxypyridine are described in U.S. Pat. No. 3,681,369. And 2-amino-trifluoromethylhalogenopyridine is described in U.S. Pat. No. 4,349,681.

The pyridine compound of this invention is different in chemical structure from such known pyridine derivatives and has a novel utility.

Also amino-trifluoromethylpyridines are described generally in U.S. Pat. No. 3,787,420, however the pyridine compounds of this invention are not described concretely therein.

SUMMARY OF THE INVENTION

An object of the present invention is to provide at least one amino-trifluoromethylpyridine compound selected from the group consisting of 3-amino-5-trifluoromethylpyridine, 2-amino-4-trifluoromethylpyridine, and 2-amino-4,6-bis(trifluoromethyl)pyridine.

Another object of the present invention is to provide a process for preparing the amino-trifluoromethylpyridine compound by reacting at least one halogeno-trifluoromethylpyridine compound selected from the group consisting of 3-halogeno-5-trifluoromethylpyridine, 2-halogeno-4-trifluoromethylpyridine, and 2-halogeno-4,6-bis(trifluoromethyl)pyridine, with ammonia at a temperature of 50° to 200° C. Although a halogen atom constituting the halogeno-trifluoromethylpyridine compound includes a fluorine atom, a chlorine atom, and a bromine atom, etc., the chlorine atom is preferable.

When the process of the present invention is carried out, generally a halogeno-trifluoromethylpyridine compound and aqueous ammonia which is prepared by dissolving ammonia in water are charged in a closed vessel, e.g., an autoclave, or liquid ammonia is introduced into the halogeno-trifluoromethylpyridine compound, followed by the reaction at a temperature of 50° to 200° C., preferably, 100° to 180° C. In this reaction, a catalyst, e.g., cuprous chloride, can be added, and the amount of the catalyst added is 1 to 30 parts by weight with respect to 100 parts by weight of the halogeno-trifluoromethylpyridine compound. When the reaction temperature exceeds the above specified upper limit, the desired product tends to decompose, whereas when it is below the lower limit, the reaction does not take place sufficiently. When the aqueous ammonia is used as the ammonia, one having a concentration of 20% or more, preferably 28 to 40% is usually used. The reaction pressure reaches about 2 to 120 atm due to an increase in temperature inside the closed vessel. The amount of ammonia used is 1 mol or more, preferably 3 to 30 mols, per mol of the halogenotrifluoromethylpyridine compound. The reaction time is 5 hours or longer, preferably 5 to 100 hours.

The reaction product thus obtained is allowed to cool and usually extracted with a solvent, such as methylene chloride, benzene, diethyl ether, or the like. The solvent is then evaporated off, and if necessary, usual distillation is carried out to obtain the desired product. The desired product in the reaction product is obtained as an oily substance or crystals, and thus, impurities can be removed by the above extraction. When aqueous ammonia is used as the ammonia, the desired product may be contained in the aqueous phase of the reaction product, but the desired product can sufficiently be recovered by the above extraction.

DETAILED DESCRIPTION OF THE PREFERRED EMBODIMENTS

Detailed preparation examples of an amino-trifluoromethylpyridine compound of the present invention will be described hereinafter, which however do not limit the invention in any way.

EXAMPLE 1

Preparation of 3-amino-5-trifluoromethylpyridine 40.8 g of 3-chloro-5-trifluoromethylpyridine, 12.2 g of cuprous chloride, and 76.5 g of liquid ammonia were charged in a 300-ml autoclave, and the mixture was reacted at 150° C. for 63 hours (internal pressure: about 120 atm).

After the completion of the reaction, the mixture was allowed to cool and pourred into water to obtain the reaction product consisting of the aqueous and oily phases. The aqueous phase was separated from the reaction product, and the desired product was extracted by methylene chloride. The methylene chloride was evaporated off, and normal distillation was carried out to obtain 25.3 g of 3-amino-5-trifluoromethylpyridine (boiling point: 105.5° to 106° C./11 mmHg).

EXAMPLE 2

Preparation of 2-amino-4-trifluoromethylpyridine 14.5 g of 2-chloro-4-trifluoromethylpyridine and 108 ml of 28% aqueous ammonia were charged in a 200-ml autoclave, and the mixture was reacted at 180° C. for 10 hours (internal pressure: about 20 atm).

After the completion of the reaction, the reaction system was allowed to cool. The resultant crystals were washed with water and dried, thus obtaining 10.2 g of 2-amino-4-trifluoromethylpyridine (melting point: 69° to 70° C.).

EXAMPLE 3

Preparation of 2-amino-4,6-bis(trifluoromethyl)pyridine 25 g of 2-chloro-4,6-bis(trifluoromethyl)pyridine and 85 g of 40% aqueous ammonia were charged into a 200-ml autoclave, and the mixture was reacted at 150° C. for 5 hours (internal pressure: about 26 atm).

After the completion of the reaction, the reaction system was allowed to cool. The resultant crystals were washed with water and dried, thus obtaining 16.5 g of 2-amino-4,6-bis(trifluoromethyl)pyridine (melting point: 70.8° to 71.2° C.).

The amino-trifluoromethylpyridine compound of the present invention is useful as an intermediate for the synthesis of agricultural chemicals and medicines, and examples thereof will be described below. For example, compounds Nos. 1 to 4 can be derived from the compound of the present invention by the processes described in the following reference examples.

REFERENCE EXAMPLE 1

Preparation of
N-(2,6-difluorobenzoyl)-N'-(5-trifluoromethyl-3-pyridyl)urea (compound No. 1)

1.0 g of 3-amino-5-trifluoromethylpyridine was dissolved in 5 ml of dioxane, and a solution of 1.35 g of 2,6-difluorobenzoylisocyanate in 2 ml of dioxane was dropwise added to the former solution. The reaction was carried out at room temperature for 1 hour, while stirring.

After the completion of the reaction, the reaction product was poured into about 100 ml of water to precipitate crystals. The precipitate was filtered and washed with methanol, followed by drying, thus obtaining 1.73 g of N-(2,6-difluorobenzoyl)-N'-(5-trifluoromethyl-3-pyridyl)urea (melting point: 233° to 235° C.).

REFERENCE EXAMPLE 2

Preparation of
N-(2,6-difluorobenzoyl)-N'-(4-trifluoromethyl-2-pyridyl)urea (compound No. 2)

0.50 g of 2-amino-4-trifluoromethylpyridine was dissolved in 7 ml of dioxane, and the solution was dropwise added to a solution of 0.56 g of 2,6-difluorobenzoylisocyanate in 7 ml of dioxane. The reaction was carried out at room temperature for about 15 hours, while stirring.

After the completion of the reaction, the reaction product was poured into about 100 ml of water to precipitate crystals. The precipitate was filtered and washed with water, followed by drying, thus obtaining 1.0 g of N-(2,6-difluorobenzoyl)-N'-(4-trifluoromethyl-2-pyridyl)urea (melting point: 167° to 169° C.).

REFERENCE EXAMPLE 3

Preparation of
N-(2,6-difluorobenzoyl)-N'-[2,4-bis(trifluoromethyl)-6-pyridyl]urea (compound No. 3)

2.2 g of 2-amino-4,6-bis(trifluoromethyl)pyridine was dissolved in 10 ml of dioxane, and the solution was dropwise added to a solution of 1.9 g of 2,6-difluorobenzoylisocyanate in 20 ml of dioxane. The reaction was then carried out at room temperature for about 1 hour.

After the completion of the reaction, the reaction product was poured into about 200 ml of warm water at 40° to 50° C. to precipitate crystals. The precipitate was filtered and dried, thus obtaining 3.2 g of N-(2,6-difluorobenzoyl)-N'-[2,4-bis(trifluoromethyl)-6-pyridyl]urea (melting point: 151.5° to 152.5° C.).

REFERENCE EXAMPLE 4

Preparation of
N-[2,4-bis(trifluoromethyl)-6-pyridyl]-2,6-dinitro-3-chloro-4-trifluoromethylaniline (compound No. 4)

1.5 g of 2-amino-4,6-bis(trifluoromethyl)pyridine was dissolved in 30 ml of dioxane, and 1.5 g of potassium hydroxide powder was added thereto while stirring. Thereafter, 2.3 g of 2,4-dichloro-3,5-dinitrobenzotrifluoride was added to the former mixture, and the resultant mixture was reacted for about 15 hours.

After the completion of the reaction, the reaction product was poured into a dilute sulfuric acid solution and extracted with methylene chloride. The extracted phase was washed with water and dried to evaporate the solvent, followed by crystallization. The resultant crystals were washed with hexane, followed by drying, thus obtaining 2.0 g of the desired product (melting point: 169° to 170° C.).

Compounds Nos. 1 to 4 derived from the aminotrifluoromethylpyridine compounds are useful as pesticides. Reference test examples of compounds Nos. 1 to 4 will be described below.

REFERENCE TEST EXAMPLE 1

Pieces of cabbage leaves were immersed in an aqueous solution which had been prepared by dispersing an effective component compound in water and adjusting its effective component concentration to 100 ppm, and the leaf pieces were then air-dried. Wet filter paper was placed in a petri dish (diameter: 9 cm), and the leaf pieces were put therein. The second and third instar larvae of a diamondback moth (*Plutella xylostella*) were released onto the cabbage leaves. The petri dish was capped and left in an air-conditioned vessel with illumination at 28° C. The numbers of alive and dead insects were counted 8 days later, and a mortality rate was calculated by the following formula to obtain the results shown in Table 1 below:

TABLE 1

| Mortality rate = 100 × (the number of dead insects)/the number of released insects) | |
|---|---|
| Compound No. | Mortality Rate (%) |
| 1 | 100 |
| 2 | 100 |
| 3 | 100 |

REFERENCE TEST EXAMPLE 2

Following the same procedures as in Reference Test Example 1, the test was carried out, except that the effective component concentration of the aqueous solution was altered from 100 ppm to 10 ppm and the 2nd to 3rd instar larvae of the diamondback moth were replaced with 2nd to 3rd instar larvae of a common cutworm (*Spodoptera litura*), and the results shown in Table 2 below were obtained.

TABLE 2

| Compound No. | Mortality Rate (%) |
|---|---|
| 1 | 100 |
| 2 | 100 |
| 3 | 100 |

REFERENCE TEST EXAMPLE 3

When a cucumber seedling (Suyo type) which had been grown in a clay pot having a diameter of 9 cm, reached the 1-leaf stage, 10 ml of an aqueous solution, in which a concentration of an effective component compound was adjusted to 100 ppm, was sprayed thereto using a spray gun. After the plant was left in a greenhouse at 24 to 25° C. for 24 hours, disks of *Batrytis cinerea* (agar punching) which had been preliminarily cultured on a potato-dextrose-agar medium (PDA medium) were placed on the leaves of the cucumber plant to inoculate it. Three days later, the spot length was evaluated, and the pest control ratio was calculated by the following formula, thus obtaining the following result.

| Pest Control Ratio (%) = {1 - (spot length in treated plot)/(spot length in untreated plot)} × 100 | |
|---|---|
| Compound No. | Pest Control Ratio (%) |
| 4 | 100 |

REFERENCE TEST EXAMPLE 4

When a cucumber seedling (Suyo type), which had been grown in a clay pot having a diameter of 9 cm, reached the 2-leaf stage, 20 ml of an aqueous solution in which a concentration of an effective component compound was adjusted to 100 ppm was sprayed thereto using a spray gun. After the plant was left in a greenhouse at 24° to 25° C. for 24 hours, a *Pseudoperonespora cubensis* spore suspension was sprayed and inoculated. Six days after the inoculation, the number of spots on the first leaf was counted, and the pest control ratio was calculated by the following formula, thus obtaining the following result.

| Pest Control Ratio (%) = {1 - (the number of spots in treated plot)/(the number of spots in untreated plot)} × 100 | |
|---|---|
| Compound No. | Pest Control Ratio (%) |
| 4 | 100 |

While the invention has been described in detail and with reference to specific embodiments thereof, it will be apparent to one skilled in the art that various changes and modifications can be made therein without departing from the spirit and scope thereof.

What is claimed is:

1. An amino-trifluoromethylpyridine compound selected from the group consisting of 3-amino-5-trifluoromethylpyridine, 2-amino-4-trifluoromethylpyridine, and 2-amino-4,6-bis(trifluoromethyl)pyridine.

2. A compound according to claim 1, wherein the amino-trifluoromethylpyridine compound is 3-amino-5-trifluoromethylpyridine.

3. A compound according to claim 1, wherein the amino-trifluoromethylpyridine compound is 2-amino-4-trifluoromethylpyridine.

4. A compound according to claim 1, wherein the amino-trifluoromethylpyridine compound is 2-amino-4,6-bis(trifluoromethyl)pyridine.

* * * * *